US011486948B2

United States Patent
Leinhard

(10) Patent No.: US 11,486,948 B2
(45) Date of Patent: Nov. 1, 2022

(54) MRI METHOD FOR CALCULATING A PROTON DENSITY FAT FRACTION

(71) Applicant: AMRA Medical AB, Linköping (SE)

(72) Inventor: Olof Dahlqvist Leinhard, Linköping (SE)

(73) Assignee: AMRA MEDICAL AB, Linköping (SE)

( * ) Notice: Subject to any disclaimer, the term of this patent is extended or adjusted under 35 U.S.C. 154(b) by 348 days.

(21) Appl. No.: 16/631,741

(22) PCT Filed: Feb. 23, 2018

(86) PCT No.: PCT/EP2018/054488
§ 371 (c)(1),
(2) Date: Jan. 16, 2020

(87) PCT Pub. No.: WO2019/015810
PCT Pub. Date: Jan. 24, 2019

(65) Prior Publication Data
US 2020/0174090 A1    Jun. 4, 2020

(30) Foreign Application Priority Data
Jul. 17, 2017    (EP) .................................... 17181641

(51) Int. Cl.
*G01V 3/00*    (2006.01)
*G01R 33/48*    (2006.01)
(Continued)

(52) U.S. Cl.
CPC ....... *G01R 33/4828* (2013.01); *G01R 33/485* (2013.01); *G01R 33/50* (2013.01); *G01R 33/5602* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 9,194,925 B2    11/2015    Zhong et al.

FOREIGN PATENT DOCUMENTS

JP    2014-091051 A    5/2014

OTHER PUBLICATIONS

E-Space English Abstract for JP 2014-091051 A.
(Continued)

*Primary Examiner* — Walter L Lindsay, Jr.
*Assistant Examiner* — Frederick Wenderoth
(74) *Attorney, Agent, or Firm* — Kagan Binder, PLLC

(57) ABSTRACT

The present invention relates to a method of calculating a proton density fat fraction, PDFF, from a water and fat separated magnetic resonance imaging, MRI, based on fat-referenced lipid quantification in a region of interest (ROI) and using determination of a reference tissue. The method comprises the step of determining: $F \cdot \beta_f / R$, wherein F is the fat signal in the ROI provided from the MRI, $\beta_f$ is a function providing a ratio between T1 saturation values of the fat signals in the reference tissue and in the ROI; and R is a representation of the sum of fat and water signals on an intensity scale where the saturation of each of the fat and water signals equals the saturation of fat in the reference tissue.

22 Claims, 1 Drawing Sheet

(51) Int. Cl.
    *G01R 33/485*    (2006.01)
    *G01R 33/50*    (2006.01)
    *G01R 33/56*    (2006.01)
(58) Field of Classification Search
    USPC ........................................................ 324/307
    See application file for complete search history.

(56) References Cited

OTHER PUBLICATIONS

Donato et al., "Liver MRI: From basic protocol to advanced techniques", European Journal of Radiology, No. 93, pp. 30-39, May 2017, (10 pages).

Meisamy et al., "Quantification of Hepatic Steatosis with T1-independent, T2*-corrected MR Imaging with Spectral Modeling of Fat: Blinded Comparison with MR Spectroscopy", Radiology, vol. 258, No. 3, pp. 767-775, Mar. 2011, (9 pages).

Hines et al., "T1 Independent, Corrected Chemical Shift Based Fat-Water Separation With Multi-peak Fat Spectral Modeling Is an Accurate and Precise Measure of Hepatic Steatosis", Journal of Magnetic Resonance Imaging, vol. 33, No. 4, pp. 873-881, Apr. 2011, (20 pages).

Gee et al., "Validation of Bone Marrow Fat Quantification in the Presence of Trabecular Bone Using MRI", Journal of Magnetic Resonance Imaging, vol. 42, No. 2, pp. 539-544, Aug. 2015, (14 pages).

Hines et al., "Quantification of Hepatic Steatosis with 3-T MR Imaging: Validation in ob/ob Mice", Radiology, vol. 254, No. 1, pp. 119-128, Jan. 2010, (10 pages).

Reeder et al., "Quantitative Assessment of Liver Fat with Magnetic Resonance Imaging and Spectroscopy", Journal of Magnetic Resonance Imaging, vol. 34, No. 4, pp. 729-749, Oct. 2011, (41 pages).

Tang et al., "Nonalcoholic Fatty Liver Disease: MR Imaging of Liver Proton Density Fat Fraction to Assess Hepatic Steatosis1", Radiology, vol. 267, No. 2, pp. 422-431, May 2013, (10 pages).

Peterson et al., "Fat Quantification in Skeletal Muscle Using Multigradient-Echo Imaging: Comparison of Fat and Water References", Journal of Magnetic Resonance Imaging, vol. 43, No. 1, pp. 203-212, May 2015, (10 pages).

Peterson et al., "Relaxation Effects in MRI-Based Quantification of Fat Content and Fatty Acid Composition", Magnetic Resonance in Medicine, vol. 72, No. 5, pp. 1320-1329, Oct. 2013, (10 pages).

International Search Report for International Application No. PCT/EP2018/054488, dated Jun. 11, 2018 (7 pages).

Indian Office Action for Indian Application No. 202027001533, dated Feb. 10, 2022, (6 pages).

Idilman et al., "Hepatic Steatosis: Quantification by Proton Density Fat Fraction with MR Imaging versus Liver Biopsy," Radiology, vol. 267, No. 3, pp. 767-775, 2013, (9 pages).

Ding et al., "Usefulness of two-point Dixon fat-water separation technique ingadoxetic acid-enhanced liver magnetic resonance imaging," World Journal of Gastroenterol, vol. 21, No. 16, pp. 5017-5022, 2015, (10 pages).

MRI METHOD FOR CALCULATING A PROTON DENSITY FAT FRACTION

CROSS-REFERENCE TO RELATED APPLICATIONS

This application claims priority to International Application No. PCT/EP2018/054488, filed Feb. 23, 2018 and titled "MRI METHOD FOR CALCULATING A PROTON DENSITY FAT FRACTION," which in turn claims priority from a European Patent Application having serial number 17181641.6, filed Jul. 17, 2017, titled "CALCULATION OF T2* CORRECTED PDFF," both of which are incorporated herein by reference in their entireties.

TECHNICAL FIELD

The present disclosure relates to calculation of proton density fat fraction (PDFF) magnetic resonance imaging (MRI) based on fat-referenced lipid quantification.

BACKGROUND

Non-alcoholic fatty liver disease (NAFLD), a range of diseases characterized by steatosis, is associated with metabolic syndrome, diabetes, and obesity (Ekstedt et al., 2006; Ertle et al., 2011) and can lead to advanced fibrosis, cirrhosis, and hepatocellular carcinoma (Ekstedt et al., 2006; Wattacheril et al., 2012). Non-alcoholic steatohepatitis, a more serious form of NAFLD, is now the single most common cause of liver disease in developed countries (Sanyal, 2011; Misra et al., 2009) and is associated with high rates of morbidity and mortality. The evaluation and grading of hepatocellular fat in patients with NAFLD usually requires a liver biopsy and histology. However, as liver biopsy is an expensive, invasive, and painful procedure that is sensitive to sampling variability (Hubscher, 2006; Wieckowska et al. 2008), imaging modalities, including magnetic resonance spectroscopy (MRS) and MRI, are frequently being adopted to determine proton density fat fraction (PDFF). PDFF-MRS is a noninvasive and accurate method for quantification of hepatic fat content, but it has proven difficult to implement in clinical practice owing to its expense and dependence on specific expertise. Further, the method only gives a local estimate of the liver fat content (Reeder et al., 2010). Multi-echo MRI-determined PDFF imaging provides non-local, quantitative, standardized measurements of hepatic fat that is reproducible and correlates closely with MRS (Noureddin 2013; Kamg 2011), liver biopsy (Tang et al., 2013) and ex vivo measurements (Bannas et al., 2015).

Traditional quantitative fat-fraction analysis using the two point Dixon (2PD) technique, which is based on acquisition of out-of-phase and in-phase images, has been shown to be useful to evaluate hepatic fat (Dixon, 1984; Glover, 1991; Qayyum et al., 2005; Pilleul et al., 2005; Reeder et al., 2005; Reeder & Sirlin, 2010). The disadvantage of 2PD in relation to multi-echo Dixon is that T2* has to be determined in a separate experiment. But, in essence, both dual and multi echo Dixon shares the same confounding factors that influence MRI signal intensity, including $T_2^*$ decay, spectral complexity of hepatic fat, and $T_1$-saturation bias (Reeder et al., 2011; Chebrolu et al., 2010). While the first three factors can be reduced through signal modeling, $T_1$-saturation bias is commonly avoided using a low flip angle since the alternative, long repetition times, results in unfeasible breath-hold times. However, a low flip angle is associated with a low signal-to-noise-ratio (SNR), leading to reduced sensitivity in liver PDFF imaging (Johnson et al., 2014). This complicates the trade-off between image voxel size, breath-hold length, and SNR. Furthermore, as the SNR decreases, proper coil positioning becomes more important, especially in obese patients, and this makes clinical translation of the technique more difficult.

By increasing the flip angle, and thereby transforming the acquisition into a $T_1$-saturated state, the trade-off between voxel size, breath-hold length, and desired level of SNR becomes less critical (Kühn et al., 2014). However, the $T_1$ weighting causes a bias in the measured signals unless corrected (Fleysher et al., 2009). It is possible to adaptively measure and compensate for the $T_1$ bias using a more complex experiment, as has been demonstrated by Kuhn and colleagues (Kuhn et al., 2014). Applying such correction to three-dimensional (3D) acquisitions is straightforward if the $T_1$ values of the fat and water tissue are well characterized. Nevertheless, the specific characteristics of the MR pulse sequence implementation and uncertainty in quantification of the $T_1$ of water and fat may influence the validity of the signal equations and lead to residual $T_1$ bias.

Fat-referenced lipid quantification allows fat quantification in $T_1$-weighted Dixon imaging, and was originally introduced by Hu and colleagues and Dahlqvist Leinhard and colleagues (Hu and Nayak, 2008; Dahlqvist Leinhard et al., 2008). This quantification method calibrates the observed signal intensities of the water and fat images using the lipid signal in pure adipose tissue. This transforms the Dixon images into a common intensity scale where a value of 1 in the fat image corresponds to an adipose tissue concentration of 100%. The invariability to the T1 weighting has been shown by Peterson et al. (Peterson et al., 2016). In that study, intramuscular adipose tissue quantification using the fat-referenced technique was validated against conventional low-flip-angle PDFF estimation with a very high agreement between the methods. Recently, Andersson and colleagues further validated the fat-referenced technique in whole-body imaging at both 1.5 T and 3.0 T for bias field estimation in skeletal muscle and liver tissue (Andersson et al., 2015). Further, Heba and colleagues determined that the accuracy of magnitude-based MRI for estimating hepatic PDFF using MRS as a reference was unchanged when using different numbers of echoes and was unaffected by possible subject-based confounders (Heba et al., 2016).

SUMMARY

As discussed above, there is a need for a framework for calculation of PDFF of for instance a liver. It is an object of the present invention to provide such framework for calculation of PDFF based on $T_1$-weighted two-point and multipoint Dixon imaging according to the appended independent claims. Embodiments of the present invention are provided by the accompanying independent claims. The present invention thereby provides technology for accurate estimation of organ PDFF using fat-referenced Dixon imaging, either via correction using the saturation ratio between the fat and water signal, or by direct use of fat estimates obtained following fat-referencing. This is especially relevant for estimation of liver PDFF for diagnosis and treatment of decreases as discussed above.

By calculating a PDFF it may be meant that in the method according to the present invention the reconstruction of fat and water images may, or may not, be corrected for $T_2^*$ effects and/or spectral dispersion effects due to characteristics of the lipid spectrum, or the reconstruction.

The PDFF calculation apparatus configured to perform the PDFF calculations may be constituted by a computer comprising the necessary computer executable program and provided with the necessary input for the calculations.

The present invention and its embodiments provide that accurate proton density fat fraction (PDFF) estimation may be achieved in $T_1$-weighted fat- and water-separated imaging using the presented framework based on fat-referenced fat quantification. The present invention provides that two-point Dixon (2PD) magnetic resonance imaging (MRI) using simplistic reconstruction without a multispectral lipid model may be used for accurate liver PDFF estimation using fixed T2* correction. This may further be improved by taking the individual T2* values of the liver water signal into account. But this is also applicable to other organs in the human body.

The fat-referenced quantification technique shows much lower sensitivity to T2* effects in 2PD PDFF calculations compared to the 2PD fat fraction technique. This lowered sensitivity to T2* relaxation is achieved because the fat referenced calculations do not include the water signal in the denominator.

The present invention provides that PDFF may be accurately estimated using T1 saturation corrected 10PD acquisitions using the suggested approach. Limits of agreement of ±1.41% for liver PDFF acquired with different sequences, in different breath holds, and with different acquisition coils in the datasets fulfilling strict quality control and ±1.44% in the analysis including all datasets may be achieved with the present invention, which are lower than what is commonly observed using other state of the art implementations.

The findings of using the present invention may be compared with those of the recent study by Heba and colleagues, in their retrospective analysis of 506 adults with non-alcoholic fatty liver disease (NAFLD), where liver PDFF was estimated using unenhanced 3.0T MRI, using right liver lobe magnetic resonance spectroscopy (MRS) as a reference (Heba et al. 2016). In this previous study, PDFF MRI findings were in close agreement with magnetic resonance spectroscopy (MRS), with the two-echo method based on fat fraction measurement with spectral correction but without T2* correction being least accurate. (Heba et al. 2016).

The present invention provides an alternative way to compensate for effects caused by the hepatic lipid spectrum. Correction of the lipid spectrum based on the acquired data, is normally a complex process, especially as the analysis also involves estimation of lipid $T_2$* and water $T_2$* relaxation (Qayyum et al. 2005; Reeder et al. 2011; Hu et al. 2011). Here, no assumptions have been made about the details of the lipid spectrum model. Using the methods described herein, the only basic assumptions made are that in-phase and opposite-phase imaging creates a highly specific contrast for fat and water, and that the effects on the observed lipid signal caused by the lipid spectrum are similar in both the reference adipose tissue and in the liver tissue.

According to a first aspect of the invention, a method of calculating a proton density fat fraction, PDFF, from a water, W, and fat, F, separated magnetic resonance imaging, MRI, based on fat-referenced lipid quantification in a region of interest (ROI) and using determination of a reference tissue is provided. The method comprises the step of determining PDFF as:

$$\frac{F \cdot \beta_f}{R}$$

wherein

F is the fat signal in the ROI provided from the MRI, $\beta_f$ is a function providing a ratio between T1 saturation values of the fat signals in the reference tissue and in the ROI; and R is a representation of the sum of fat and water signals on an intensity scale where the saturation of each of the fat and water signals equals the saturation of fat in the reference tissue.

The method may be described as comprising the fat signal in the ROI provided from the MRI multiplied with $\beta_f$ being a function providing a ratio between T1 saturation value of the fat signals in the reference tissue and in the ROI, wherein the product thereof is divided with R being a representation of the signal intensity of the sum of fat and water on an intensity scale where fat and water are saturated with the saturation level only affecting the fat signal extrapolated from the reference tissue.

In one embodiment, the method may further comprise a step of determining the T1 saturation value of the fat signal in the reference tissue. Alternatively, such determination is premade and the method may comprise a step of receiving a T1 saturation value of the fat signal in the reference tissue. Further, the method may in one embodiment comprise a step of determining a T1 saturation value of the fat signal in the ROI, to be used for $\beta_f$ in the determination of PDFF, or alternatively a step of receiving such T1 saturation value of the fat signal in the ROI.

In one embodiment, the method may comprise a step of receiving a value of R as defined above, for the determination of PDFF. Alternatively, the method may comprise a step of receiving input for the determination of R, and a step of determining R based on said input.

In one embodiment, R may provide a quota between $F_{ref}$ and $PDFF_{ref}$ such that the method comprises the step of determining PDFF as:

$$\frac{F}{F_{ref}} \cdot \beta_f \cdot PDFF_{ref}$$

wherein $F_{ref}$ is the fat signal in the reference tissue; and $PDFF_{ref}$ is the PDFF of the reference tissue provided by a separate experiment of the reference tissue or by a predetermined constant.

The method according to this embodiment may further be described as the quota between F and $F_{ref}$ being the fat signal in the reference tissue, multiplied with $\beta_f$ and $PDFF_{ref}$ being the PDFF of the reference tissue provided by a separate experiment of the reference tissue or by a predetermined constant. The values of $PDFF_{ref}$ and $F_{ref}$ may in one embodiment be received in a step of the method to be used for the determination of PDFF.

In another embodiment, the T1 saturation values of the fat signal in the reference tissue and in the ROI may be equal, providing $\beta_f=1$.

In a further embodiment, the PDFF may be determined from a fat-referenced two-point Dixon acquisition without previous correction for $T_2$* relaxation effects, and the water signal in the reference tissue, $W_{ref}$, may be low such that a resulting value when $W_{ref}$ is multiplied with a resulting $T_2$* relaxation effect provides an approximation that the water signal in the ROI equals an observed water signal in the ROI, $W_{2PD}$, being a reconstruction of the water signal from the MRI in the ROI using two-point Dixon acquisition, providing the PDFF to be determined as $$\frac{F_{2PD} - W_{2PD} \cdot \frac{e^{-T_{ip}/T_{2,w}^*} - e^{-T_{op}/T_{2,w}^*}}{2}}{F_{2PD,ref}} \cdot \beta_f \cdot PDFF_{ref}$$

wherein $F_{2PD}$ is the observed fat signal in the ROI, being a reconstruction of the fat signal from the MRI in the ROI using two-point Dixon acquisition;

$T_{ip}$ is a constant of the echo time of the in-phase (IP) component comprising water plus fat signal of the water and fat signals from the MRI in the ROI;

$T_{2*w}$ is the $T_2^*$ relaxation effect of water in the ROI resulting from the two-point Dixon analysis;

$T_{op}$ is a constant of the echo time of the out-of-phase (OP) component comprising the difference between the water and fat signals from the MRI in the ROI; and $F_{2PD, ref}$ is the observed fat signal of the reference tissue, being a reconstruction of the fat signal from the MRI in the reference tissue using two-point Dixon acquisition. In one embodiment, the method may comprise a step of receiving the $F_{2PD}$ and $F_{2PD, ref}$ signal values to be used for the PDFF determination. In one embodiment, the method may comprise a step of receiving the $T_{op}$ and $T_{ip}$ time values to be used for the PDFF determination. In one embodiment, the method may comprise a step of receiving the $T_{2*w}$ value to be used for the PDFF determination.

In one embodiment, the $T_2^*$ relaxation effect value may be determined in a separate experiment.

In another embodiment, the $T_2^*$ relaxation effect value may be set as a constant based on a population mean.

In a further embodiment, $\beta_f$ may be the quota of $$\sin(\alpha)\frac{1-e^{-T_R/T_{1f,ref}}}{1-\cos\alpha(1-e^{-T_R/T_{1f,ref}})} \text{ and } \sin(\alpha)\frac{1-e^{-T_R/T_{1f,ROI}}}{1-\cos\alpha(1-e^{-T_R/T_{1f,ROI}})},$$

wherein $\alpha$ is the effective flip angle in the MRI acquisition, $T_R$ is the repetition time, $T_{1f,ref}$ is the T1 value for the fat signal in the reference tissue, and $T_{1f,ROI}$ is the T1 value for the fat signal in the ROI. In one embodiment, the method may comprise a step of receiving the $T_R$, $T_{1f,ref}$ and $T_{1f,ROI}$ values to be used for the PDFF determination.

In another embodiment, the $F_{ref}$ may be determined as a weighted interpolation of the fat signal in the reference tissue. Further, to provide such weighted interpolation of the fat signal in the reference tissue, a method as presented in "Romu T, Borga M, Dahlqvist Leinhard O. MANA—multiscale adaptive normalized averaging. In: Proceedings of the IEEE International Symposium on Biomedical Imaging: From Nano to Macro, Chicago, Ill., USA, 2011. pp 361-364" may be used.

In one embodiment, R may be defined as $F\cdot\beta_f + W\cdot\beta_w$, and wherein the T1 saturation value of the fat signal in the reference tissue and in the ROI is equal, providing $\beta_f=1$, providing the method comprising the step of determining PDFF as $$\frac{F}{F + W \cdot \beta_w}$$

wherein

W is the water signal in the ROI provided by the MRI; and $\beta_w$ is a function providing a ratio between the T1 saturation value of the fat signal in the reference tissue and the T1 saturation value of the water signal in the ROI. In one embodiment, the method may further comprise a step of determining the T1 saturation value of the fat signal in the reference tissue. Alternatively, such determination is premade and the method may comprise a step of receiving a T1 saturation value of the fat signal in the reference tissue. Further, the method may in one embodiment comprise a step of determining a T1 saturation value of the fat signal in the ROI, to be used for $\beta_w$ in the determination of PDFF. Alternatively, such determination is premade and the method may comprise a step of receiving a T1 saturation value of the fat signal in the ROI.

In a further embodiment, $\beta_w$ may be determined in a separate experiment by determining $$\min_{\beta_w}\left(\sum_{Measurements}\left(\frac{F}{F+W\cdot\beta_w} - PDFF_{ex}\right)^2\right)$$

wherein $PDFF_{ex}$ is the proton density fat fraction measured in a separate experiment. The $PDFF_{ex}$ measured in a separate experiment may preferably, but not necessarily, be made in the same subject as the PDFF calculation in which the $\beta_w$ to be determined is to be used.

In a yet further embodiment, PDFF may be provided by a separate 2-point Dixon experiment. The equation to determine $\beta_w$ may then be provided by determining $$\min_{\beta_w}\left(\sum_{Measurements}\left(\frac{F}{F+W\cdot\beta_w} - PDFF_{2PD}\right)^2\right)$$

According to a second aspect of the invention, a proton density fat fraction, PDFF, calculation apparatus is provided, wherein the calculation apparatus comprises a receiver and a processor. The receiver may be configured to receive a water, W, and fat, F, separated magnetic resonance imaging, MRI. The processor may be configured to, based on the received water and fat separated MRI, and based on fat-referenced lipid quantification in a region of interest (ROI) and using determination of a reference tissue, determine the PDFF as $$\frac{F \cdot \beta_f}{R}$$

wherein

F is the fat signal in the ROI provided from the MRI, $\beta_f$ is a function providing a ratio between T1 saturation values of the fat signals in the reference tissue and in the ROI; and R is a representation of the sum of fat and water signals on an intensity scale where the saturation of each of the fat and water signals equals the saturation of fat in the reference tissue. The receiver and the processor may further be configured to receive entities and perform determinations according to any of the embodiments described above. As seen in FIG. 3, the PDFF calculation apparatus 10 may receive input from a MRI source 20. The MRI source 20 may provide water and fat separated MR data for the ROI and the reference tissue. The PDFF calculation apparatus 10 may be a computer configured to perform the calculations according to any of the embodiments above.

BRIEF DESCRIPTION OF THE DRAWINGS

The invention will in the following be described in more detail with reference to the enclosed drawings, wherein.

DESCRIPTION OF EMBODIMENTS

Figure 1:
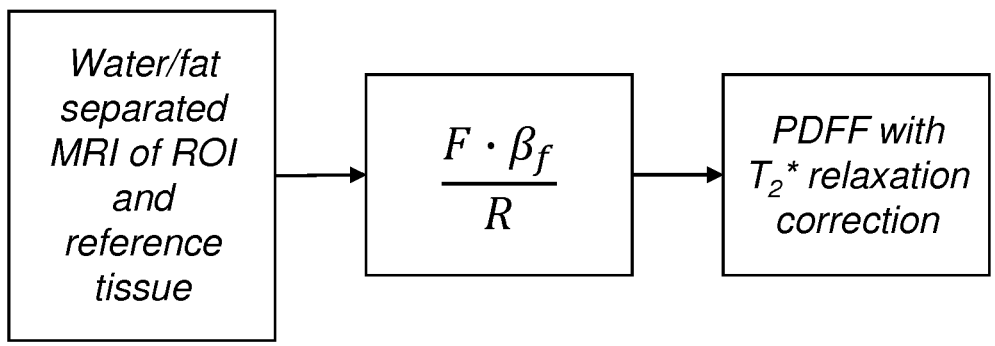
FIG. 1 shows a schematic block view of a method according to an embodiment of the present invention.

The present invention will be described more fully hereinafter according to preferred embodiments of the invention. This invention may, however, be embodied in many different forms and should not be construed as limited to the embodiments set forth herein; rather, these embodiments are provided so that this disclosure will be thorough and complete, and will fully convey the scope of the invention to those skilled in the art.

Signal Model

In spoiled gradient echo water-fat separated image reconstruction after taking $T_2^*$ and lipid spectrum effects into account, the water (W) and fat (F) signals can be represented by the following equations:

$$W = W_{unsat} \cdot \sin(\alpha) \frac{1 - e^{-T_R/T_{1w}}}{1 - \cos\alpha(1 - e^{-T_R/T_{1w}})} = W_{unsat} \cdot s_w \text{ and} \quad \text{[equation 1]}$$

$$F = F_{unsat} \cdot \sin(\alpha) \frac{1 - e^{-T_R/T_{1f}}}{1 - \cos\alpha(1 - e^{-T_R/T_{1f}})} = F_{unsat} \cdot s_f, \quad \text{[equation 2]}$$

where $W_{unsat}$ and $F_{unsat}$ are the unsaturated water and fat signals, and $s_w$ and $s_f$ are the water- and fat-saturation factors that are dependent on the local flip angle $\alpha$, the repetition time TR and the tissue dependent $T_1$ values, $T_{1w}$ and $T_{1f}$, for water and fat. Note that the exact value of $\alpha$ is unknown as it is dependent on prescan performance and on the characteristics of the radiofrequency pulse profile.

To quantify the fat content of a tissue, the unsaturated $F_{unsat}$ is insufficient as it is dependent on a range of unknown factors, besides the number of fat protons. Proton density fat fraction (PDFF) is a quantitative fat-content technique that is invariant to these unknown factors. In PDFF imaging $F_{unsat}$ is calibrated using a unsaturated in-phase signal reference, $IP_{unsat} = F_{unsat} + W_{unsat}$, e.g. PDFF is defined as:

$$PDFF = \frac{F_{unsat}}{IP_{unsat}}. \quad \text{[equation 3]}$$

Because the multiplicative factors are identical in $F_{unsat}$ and $IP_{unsat}$, PDFF is the fraction of MRI visible fat protons in relation to the sum of MRI visible fat and water protons. Furthermore, as PDFF is based on the unsaturated MRI signals, the acquisition parameters must be set such that $s_w \approx s_f$, e.g. by choosing a low flip angle. Alternatively, additional images need to be collected to determine the ratio between and $s_w$ and $s_f$.

An alternative quantitative technique is fat-referenced MRI where F is calibrated using a fat signal $F_{ref}$ (Romu et al., 2011; Dahlqvist Leinhard et al., 2008). The benefit is that this measurement is invariant to the water and fat saturations given that $F_{ref}$ is affected by the same $s_f$ as F. However, the fat-referenced signal corresponds to the number of fat protons in the measurement point relative to the number of fat protons in the reference, and is thus not identical to PDFF. To translate the fat-reference signal to PDFF, assume that there exists an in-phase reference, R, which saturates with a fat saturation factor, $s_{f,R}$, e.g.:

$$R = IP_{unsat} s_{f,R}. \quad \text{[equation 4]}$$

Then, the PDFF equation can be expressed as:

$$PDFF = \frac{F_{unsat}}{IP_{unsat}} = \frac{F}{R} \frac{s_{f,R}}{s_f} = \frac{F}{R} \beta_f, \quad \text{[equation 5]}$$

where the factor $$\beta_f = \frac{s_{f,R}}{s_f}, \quad \text{[equation 6]}$$

corrects for any difference in saturation between the measured fat signal and the reference. Also note that if the saturation of R is similar to that of the fat signal, then $\beta_f \approx 1$.

Relating the Fat-Referenced Signal to PDFF

Figure 2:
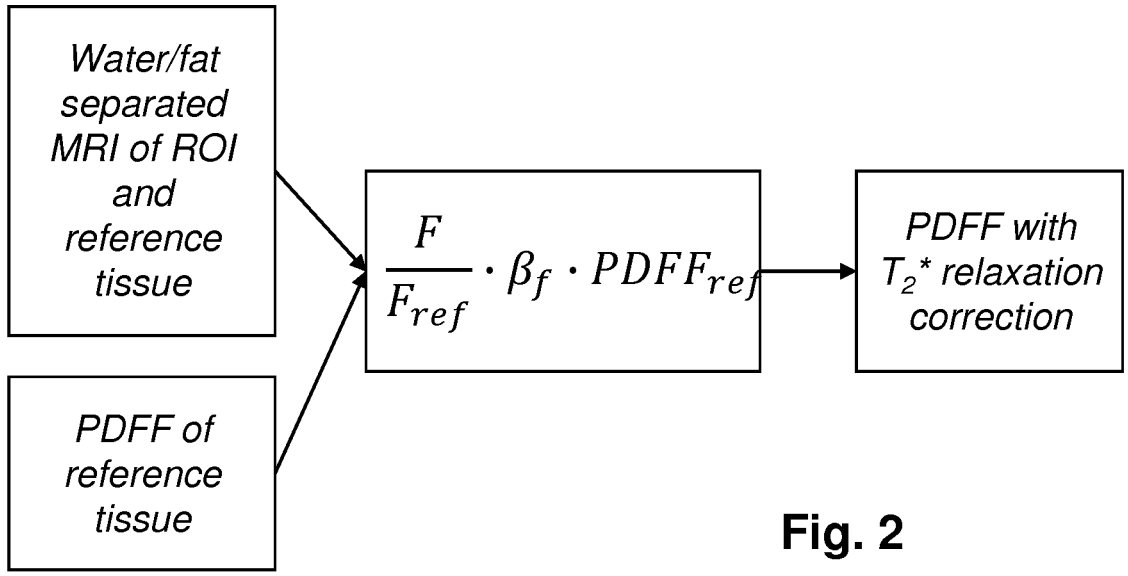
FIG. 2 shows a schematic block view of a method according to an embodiment of the present invention.

In fat-referenced lipid quantification, a signal reference is acquired from regions of pure adipose tissue within the subject and interpolated over the complete image volume (Romu et al., 2011; Dahlqvist Leinhard et al., 2008). To convert the fat-referenced signal to PDFF, let $F_{ref}$ represent the fat signal of the reference tissue, and set the saturation of R to the saturation level of $F_{ref}$, i.e. $s_{f,ref} = s_{f,R}$. Thus, the PDFF of the reference tissue is equal to $F_{ref} \cdot R^{-1}$, so $R = F_{ref} \cdot PDFF_{ref}^{-1}$, and eq. 5 describing PDFF in the measurement point can therefore be reformulated as (see FIGS. 1 and 2):

$$PDFF = \frac{F}{R} \beta_f = \frac{F}{F_{ref}} \beta_f \cdot PDFF_{ref}, \quad \text{[equation 7]}$$

where $F \cdot F_{ref}^{-1}$ is the fat-referenced signal, e.g. the raw fat signal calibrated by the interpolated fat reference signal. This is further illustrated in FIGS. 1 and 2.

The consequence of Eq. 7 is that the calibrated fat signal in the fat-referenced analysis can be converted to PDFF by adjusting for the PDFF in the adipose reference tissue and for any difference in fat saturation relative to the reference. Furthermore, if the fat saturation is similar to the reference, then the fat-referenced PDFF can be computed as:

$$PDFF = \frac{F}{F_{ref}} PDFF_{ref}. \quad \text{[equation 8]}$$

Adjusting for Effects Occurring in Two-Point Dixon (2PD) Imaging

In 2PD analysis, using simplistic reconstruction of the fat and water image components after phase-sensitive reconstruction of the OP image, the observed fat signal is given by $$F_{2PD} = \frac{IP - OP}{2} = F \cdot \frac{e^{-T_{ip}/T_{2,f}^*} \cdot d_{ip} + e^{-T_{op}/T_{2,f}^*} \cdot d_{op}}{2} + W \cdot \frac{e^{-T_{ip}/T_{2,w}^*} - e^{-T_{op}/T_{2,w}^*}}{2} = F \cdot t_f^+ + W \cdot t_w^-, \quad \text{[equation 9]}$$

where $t_f^+$ is a function of the fat $T_2^*$-relaxation, $T_{2,f}^*$, the spectral dispersion of fat, d, and the echo times $T_{op}$ and $T_{ip}$. Similarly, $t_w^-$ describes the crosstalk caused by the water signal as a function of $T_{2,w}^*$ and the echo times $T_{op}$ and $T_{ip}$. Similarly, the observed water signal is given by $$W_{2PD} = \frac{IP + OP}{2} = F \cdot \frac{e^{-T_{ip}/T_{2,f}^*} \cdot d_{ip} - e^{-T_{op}/T_{2,f}^*} \cdot d_{op}}{2} + W \cdot \frac{e^{-T_{ip}/T_{2,w}^*} + e^{-T_{op}/T_{2,w}^*}}{2} = F \cdot t_f^- + W \cdot t_w^+. \quad \text{[equation 10]}$$

Solving for the PDFF in Eq. 8, with the corresponding signal estimated using two-point Dixon imaging, gives $$PDFF_{2PD} = \frac{\frac{F_{2PD} - W_{2PD} \cdot t_w^-}{t_f^+}}{\frac{F_{2PD,ref} - W_{ref} \cdot t_{w,ref}^-}{t_{f,ref}^+}} \cdot PDFF_{ref}. \quad \text{[equation 11]}$$

Furthermore, since $F_{2PD,ref} \gg W_{ref} t_{w,ref}^-$ in adipose tissue and assuming similar $T_2^*$ effects $F_{2PD}$ and $F_{2PD,ref}$, i.e. $t_f^+ \approx t_{f,ref}^+$, Eq. 11 can be approximated to:

$$PDFF_{2PD} = \frac{F_{2PD} - W_{2PD} \cdot t_w^-}{F_{2PD,ref}} \cdot PDFF_{ref} = \frac{F_{2PD} - 0.5 \cdot W_{2PD} \cdot \left(e^{-T_{ip}/T_{2,w}^*} - e^{-T_{op}/T_{2,w}^*}\right)}{F_{2PD,ref}} \cdot PDFF_{ref}, \quad \text{[equation 12]}$$

where $T_{2,w}^*$, and $PDFF_{ref}$ are the only unknowns.

Quantification of PDFF in $T_1$-Saturated Dixon Imaging

Two different implementations for PDFF quantification in $T_1$-saturated Dixon imaging can be used.

Implementation 1. Fat-Referenced Dixon Imaging with Correction for Effects of $T_2^*$ Relaxation and Adipose Tissue Water Concentration.

Assuming $T_1$-saturated 2PD, such that the PDFF is given by Eq. 12. Furthermore, the values of $T_{2,w}^*$ and $PDFF_{ref}$ in Eq. 12 can either be determined on an individual level in a separate experiment, or assumed to be constant and set to a population mean.

Implementation 2. Water-Referenced $T_2^*$-Corrected Dixon Imaging with $T_1$-Saturation Correction Based on Fat-Referenced Dixon Imaging.

If the saturation ratio between fat and water, $\beta_w = s_f/s_w$, is known, the PDFF from a $T_1$-saturated Dixon acquisition, corrected for $T_2^*$ and spectral dispersion effects, is given by $$PDFF = \frac{F}{F + W \cdot \beta_w}. \quad \text{[equation 13]}$$

The saturation ratio $\beta_w$ can then be determined based on a separate PDFF experiment, such as the fat referenced $PDFF_{2PD}$, by minimizing the following expression with respect to $\beta_w$, $$\min_{\beta_w}\left(\sum_{All\ subjects} \left(\frac{F}{F + W \cdot \beta_w} - PDFF_{2PD}\right)^2\right). \quad \text{[equation 14]}$$

which minimizes the observed differences between PDFF in the water-referenced acquisition and $PDFF_{2PD}$ from the fat-referenced $T_2^*$-corrected 2PD acquisition.

Figure 3:
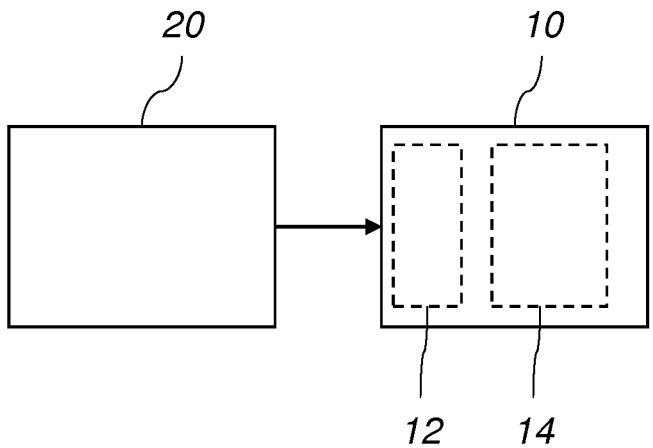
FIG. 3 shows a schematic block view of a PDFF calculation apparatus according to an embodiment of the present invention.

FIG. 3 illustrates a PDFF calculation apparatus 10 receiving input from an MRI source 20, the input being a water and fat separated MR imaging. The PDFF calculation apparatus 10 comprises a receiver 12 and a processor 14. The receiver is configured to receive the input from the MRI source 20. The processor is configured to determine the PDFF according to a method as described above. The receiver 12 may also receive input in the form of a PDFF of a reference tissue to be used in the determination by the processor.

REFERENCES

Addeman B T, Kutty S, Perkins T G, Soliman A S, Wiens C N, McCurdy C M, Beaton M D, Hegele R A, McKenzie C A. Validation of volumetric and single-slice MRI adipose analysis using a novel fully automated segmentation method. J Magn Reson Imaging 2015; 41:233-241.

Andersson T, Romu T, Karlsson A, Noren B, Forsgren M, Smedby O, Kechagias S, Almer S, Lundberg P, Borga M, Dahlqvist Leinhard O. Consistent intensity inhomogeneity correction in water-fat MRI. J Magn Reson Imaging 2015; 42(2):468-476.

Bannas P, Kramer H, Hernando D, Agni R, Cunningham A M, Mandal R, Motosugi U, Sharma S D1, Munoz del Rio A, Fernandez L, Reeder S B. Quantitative magnetic resonance imaging of hepatic steatosis: Validation in ex vivo human livers. Hepatology 2015; 62(5):1444-55.

Borga M, Thomas E L, Romu T, Rosander J, Fitzpatrick J, Dahlqvist Leinhard O, Bell J D. Validation of a fast method for quantification of intra-abdominal and subcutaneous adipose tissue for large-scale human studies. NMR Biomed 2015; 28(12):1747-53.

Chebrolu VV, Hines C D G, Yu H, Pineda A R, Shimakawa A, McKenzie C, Samsonov A, Brittain J H, Reeder S B. Independent Estimation of T2* for Water and Fat for Improved Accuracy of Fat Quantification. Mag Reson Med 2010; 63(4):849-857.

Cowin G J, Jonsson J R, Bauer J D, Ash S, Ali A, Osland E J, Purdie D M, Clouston A D, Powell E E, Galloway G J. Magnetic resonance imaging and spectroscopy for monitoring liver steatosis. J Magn Reson Imaging 2008; 28(4): 937-945.

Dahlqvist Leinhard O, Johansson A, Rydell J, Smedby Ö, Nyström F, Lundberg P, Borga M. Quantitative abdominal fat estimation using MRI. IEEE 19th International Conference on Pattern Recognition 2008; 19:1-4.

Dahlqvist Leinhard O, Dahlström N, Kihlberg J, Sandstrm P, Brismar T B, Smedby O, Lundberg P. Quantifying differences in hepatic uptake of the liver specific contrast agents Gd-EOB-DTPA and Gd-BOPTA: a pilot study. Eur Radiol 2012; 22(3):642-53.

Dixon W. Simple proton spectroscopic imaging. Radiology 1984; 153:189-194.

Eksted M, Franzen L E, Mathiesen U L, Thorelius L, Holmqvist M, Bodemar G, Kechaglas S. Long-term follow-up of patients with NAFLD and elevated liver enzymes. Hepatology 2006; 44(4):865-873.

Erlingsson S, Herard S, Dahlqvist O, Lindström T, Länne T, Borga M, Nystrom F H, Group FFS. Men develop more intraabdominal obesity and signs of the metabolic syndrome after hyperalimentation than women. Metabolism 2009; 58:995-1001.

Ertle J, Dechene A, Sowa J P, Penndorf V, Herzer K, Kar G, Schlaak J F, Gerken G, Syn W K, Canbay A. Non-alcoholic fatty liver disease progresses to hepatocellular carcinoma in the absence of apparent cirrhosis. Int J Cancer 2011; 128(10):2436-2443.

Ganna A, Ingelsson E. 5-year mortality predictors in 498, 103 U K Biobank participants: a prospective population-based study. Lancet 2015; 386:533-40.

Glover G H. Multipoint Dixon technique for water and fat proton and susceptibility imaging. J Magn Reson Imaging 1991;1:521-530.

Heba E R, Desai A, Zand K A, Hamilton G, Wolfson T, Schlein A N, Gamst A, Loomba R, Sirlin C B, Middleton M S. Accuracy and the effect of possible subject-based confounders of magnitude-based MRI for estimating hepatic proton density fat fraction in adults, using MR spectroscopy as reference. J Magn Reson Imaging. 2016; 43(2):398-406.

Hu H H, Nayak K S. Quantification of absolute fat mass using an adipose tissue reference signal model. J Magn Reson Imaging 2008; 28:1483-1491.

Hu H H, Nayak K S. Change in the Proton T1 of Fat and Water in Mixture. Magn Reson Med 2010; 63(2):494-501.

Hu H H, Li Y, Nagy T R, Goran M I, Nayak K S. Quantification of Absolute Fat Mass by Magnetic Resonance Imaging: a Validation Study against Chemical Analysis. Int J Body Compos Res 2011; 9(3):111-122.

Hubscher S G. Histological assessment of non-alcoholic fatty liver disease. Histopathology 2006; 49(5):450-465.

Karlsson A, Rosander J, Romu T, Tallberg J, Grönqvist A, Borga M, Dahlqvist Leinhard O. Automatic and quantitative assessment of regional muscle volume by multi-atlas segmentation using whole-body water-fat MRI. J Magn Reson Imaging 2015; 41(6):1558-1569.

Kim H, Taksali S E, Dufour S, Befroy D, Goodman T R, Falk Petersen K, Shulman G I, Caprio S, Constable R T. Comparative MR study of hepatic fat quantification using single-voxel proton spectroscopy, two-point Dixon and three-point IDEAL. Magn Reson Med 2008; 59(3):521-527.

Kühn J P, Berthold F, Mayerle J, Völzke H, Reeder S B, Rathmann W, Lerch M M, Hosten N, Hegenscheid K, Meffert P J. Pancreatic Steatosis Demonstrated at MR Imaging in the General Population: Clinical Relevance. Radiology 2015; 276(1):129-36.

Ludwig U A, Klausmann F, Baumann S, Honal M, Hövener J B, König D, Deibert P, Büchert M. Whole-body MRI-based fat quantification: a comparison to air displacement plethysmography. J Magn Reson Imaging 2014; 40:1437-1444.

Misra V L, Khashab M, Chalasani N. Nonalcoholic fatty liver disease and cardiovascular risk. Curr Gastroenterol Rep 2009; 11(1):50-55.

O'Regan D P, Callaghan M F, Wylezinska-Arridge M, Fitzpatrick J, Naoumova R P, Hajnal J V, Schmitz S A. Liver fat content and T2*:simultaneous measurement by using breath-hold multiecho MR imaging at 3.0 T-feasibility. Radiology 2008; 247:550-557.

Palmer L J. U K Biobank: bank on it. Lancet 2007; 369: 1980-1982.

Peterson P, Månsson S. Simultaneous quantification of fat content and fatty acid composition using MR imaging. Magn Reson Med 2013; 69:688-697.

Peterson P, Svensson J, Månsson S. Relaxation effects in MRI-based quantification of fat content and fatty acid composition. Magn Reson Med. 2014; 72(5):1320-9.

Pilleul F, Chave G, Dumortier J, Scoazec J Y, Valette P J. Fatty infiltration of the liver. Detection and grading using dual T1 gradient echo sequences on clinical MR system. Gastroenterol Clin Biol 2005; 29(11):1143-1147.

Qayyum A, Goh J S, Kakar S, Yeh B M, Merriman R B, Coakley F V. Accuracy of liver fat quantification at MR imaging: comparison of out-of-phase gradient-echo and fat-saturated fast spin-echo techniques—initial experience. Radiology 2005; 237(2):507-511.

Reeder S B, Pineda A R, Wen Z, Shimakawa A, Yu H, Brittain J H, Gold G E, Beaulieu C H, Pelc N J. Iterative decomposition of water and fat with echo asymmetry and least-squares estimation (IDEAL): application with fast spin-echo imaging. Magn Reson Med 2005; 54:636-644

Reeder S B, Sirlin C B. Quantification of liver fat with magnetic resonance imaging. Magn Reson Imaging Clin N Am 2010; 18(3):337-357.

Reeder S B, Cruite I, Hamilton G, Sirlin C B. Quantitative assessment of liver fat with magnetic resonance imaging and spectroscopy. J Magn Reson Imaging 2011; 34(4): 729-749.

Romu T, Borga M, Dahlqvist Leinhard O. MANA-multi-scale adaptive normalized averaging. In: Proceedings of the IEEE International Symposium on Biomedical Imaging: From Nano to Macro, Chicago, Ill., USA, 2011. pp 361-364.

Romu T, Elander L, Leinhard O D, Lidell M E, Betz M J, Persson A, Enerbäck S, Borga M. Characterization of brown adipose tissue by water-fat separated magnetic resonance imaging. J Magn Reson Imaging 2015; 42(6): 1639-45

Rydell J, Knutsson H, Pettersson J, Johansson A, Farnebäck G, Dahlqvist O, Lundberg P, Nyström F, Borga M. Phase sensitive reconstruction for water/fat separation in MR imaging using inverse gradient. Med Image Comput Comput Assist Interv 2007; 10(Pt1):210-8.

Sanyal A J. NASH: a global health problem. Hepatol Res. 2011; 41(7):670-674.

Sharma P, Altbach M, Galons J-P, Kalb B, Martin D R. Measurement of liver fat fraction and iron with MRI and MR spectroscopy techniques. Diagn Interv Radiol 2014; 20(1):17-26.

Tang A, Tan J, Sun M, Hamilton G, Bydder M, Wolfson T, Gamst A C, Middleton M, Brunt E M, Loomba R, Lavine J E, Schwimmer J B, Sirlin C B. Nonalcoholic Fatty Liver Disease: MR Imaging of Liver Proton Density Fat Fraction to Assess Hepatic Steatosis. Radiology 2013; 267(2): 422-431.

Wattacheril J, Chalasani N. Nonalcoholic fatty liver disease (NAFLD): is it really a serious condition? Hepatology 2012; 56(4):1580-1584.

Wieckowska A, Feldstein A E. Diagnosis of nonalcoholic fatty liver disease: invasive versus noninvasive. Semin Liver Dis 2008; 28(4):386-395.

Würslin C, Machann J, Rempp H, Claussen C, Yang B, Schick F. Topography mapping of whole body adipose tissue using a fully automated and standardized procedure. J Magn Reson Imaging 2010; 31:430-439.

Yokoo T, Bydder M, Hamilton G, Middleton M S, Gamst A C, Wolfson T, Hassanein T, Patton H M, Lavine J E, Schwimmer J B, Sirlin C B. Nonalcoholic fatty liver disease: diagnostic and fat-grading accuracy of low-flip-angle multiecho gradient-recalled-echo MR imaging at 1.5 T. Radiology 2009; 251(1):67-76.

In the drawings and specification, there have been disclosed preferred embodiments and examples of the invention and, although specific terms are employed, they are used in a generic and descriptive sense only and not for the purpose of limitation, the scope of the invention being set forth in the following claims.

The invention claimed is:

1. A method of calculating a proton density fat fraction, PDFF, from a water, W, and fat, F, separated magnetic resonance imaging, MRI, based on fat-referenced lipid quantification in a region of interest (ROI) and using determination of a reference tissue, the method comprising the step of determining PDFF as:

$$\frac{F \cdot \beta_f}{R}$$

wherein

F is the fat signal in the ROI provided from the MRI, $\beta_f$ is a function providing a ratio between T1 saturation factors of the fat signals in the reference tissue and in the ROI; and R is a representation of the sum of the unsaturated fat and water signals after this sum has been saturated by the saturation factor for fat in the reference tissue.

2. A proton density fat fraction, PDFF, calculation apparatus comprising:

a receiver configured to receive a water, W, and fat, F, separated magnetic resonance imaging, MRI; and a processor configured to, based on the received water and fat separated MRI, and based on fat-referenced lipid quantification in a region of interest (ROI) and using determination of a reference tissue, determine the PDFF as $$\frac{F \cdot \beta_f}{R}$$

wherein

F is the fat signal in the ROI provided from the MRI, $\beta_f$ is a function providing a ratio between T1 saturation factors of the fat signals in the reference tissue and in the ROI; and R is a representation of the sum of the unsaturated fat and water signals after this sum has been saturated by the saturation factor for fat in the reference tissue.

3. Method according to claim 1, wherein R provides a quota between $F_{ref}$ and $PDFF_{ref}$ such that the method comprises the step of determining PDFF as:

$$\frac{F}{F_{ref}} \cdot \beta_f \cdot PDFF_{ref}$$

wherein $F_{ref}$ is the fat signal in the reference tissue; and $PDFF_{ref}$ is the PDFF of the reference tissue provided by a separate experiment of the reference tissue or by a predetermined constant.

4. The method according to claim 1, wherein the T1 saturation factors of the fat signal in the reference tissue and in the ROI are equal, providing $\beta_f=1$.

5. The method according to claim 3, wherein the PDFF is determined from a fat-referenced two-point Dixon acquisition without previous correction for $T_2^*$ relaxation effects, and wherein the water signal in the reference tissue, $W_{ref}$, is low such that a resulting value when $W_{ref}$ is multiplied with a resulting $T_2^*$ relaxation effect provides an approximation that the water signal in the ROI equals an observed water signal in the ROI, $W_{2PD}$, being a reconstruction of the water signal from the MRI in the ROI using two-point Dixon acquisition, providing the PDFF to be calculated as $$\frac{F_{2PD} - W_{2PD} \cdot \frac{e^{-T_{ip}/T_{2w}^*} - e^{-T_{op}/T_{2w}^*}}{2}}{F_{2PD,ref}} \cdot \beta_f \cdot PDFF_{ref}$$

wherein $F_{2PD}$ is the observed fat signal in the ROI, being a reconstruction of the fat signal from the MRI in the ROI using two-point Dixon acquisition;

$T_{ip}$ is a constant of the echo time of the in-phase (IP) component comprising water plus fat signal of the water and fat signals from the MRI in the ROI;

$T_{2w}^*$ is the $T_2^*$ relaxation effect of water in the ROI resulting from the two-point Dixon analysis;

$T_{op}$ is a constant of the echo time of the out-of-phase (OP) component comprising the difference between the water and fat signals from the MRI in the ROI; and $F_{2PD, ref}$ is the observed fat signal of the reference tissue, being a reconstruction of the fat signal from the MRI in the reference tissue using two-point Dixon acquisition.

6. The method according to claim 5, wherein the $T_2^*$ relaxation effect value is determined in a separate experiment.

7. The method according to claim 5, wherein the $T_2^*$ relaxation effect value is set as a constant based on a population mean.

8. The method according to claim 1, wherein the water and fat separated imaging is a spoiled gradient echo water-fat separated image reconstruction, and wherein $\beta_f$ is the quota of $$\sin(\alpha) \frac{1 - e^{-T_R/T_{1f,ref}}}{1 - \cos\alpha\left(1 - e^{-T_R/T_{1f,ref}}\right)} \text{ and } \sin(\alpha) \frac{1 - e^{-T_R/T_{1f,ROI}}}{1 - \cos\alpha\left(1 - e^{-T_R/T_{1f,ROI}}\right)},$$

wherein $\alpha$ is the effective flip angle in the MRI acquisition, $T_R$ is the repetition time, $T_{1f,ref}$ is the T1 value for the fat signal in the reference tissue, and $T_{1f,ROI}$ is the T1 value for the fat signal in the ROI.

9. The method according to claim 3, wherein the $F_{ref}$ is determined as a weighted interpolation of the fat signal in the reference tissue.

10. The method according to claim 1, wherein R is defined as $F \cdot \beta_f + W \cdot \beta_w$, and wherein the T1 saturation factor of the fat signal in the reference tissue and in the ROI is equal, providing $\beta_f=1$, providing the method comprising the step of determining PDFF as $$\frac{F}{F + W \cdot \beta_w}$$

wherein
W is the water signal in the ROI provided by the MRI; and
$\beta_w$ is a function providing a ratio between the T1 saturation factor of the fat signal in the reference tissue and the T1 saturation factor of the water signal in the ROI.

11. The method according to claim 10, wherein $\beta_w$ is determined in a separate experiment by determining $$\min_{\beta_w}\left(\sum_{Measurements}\left(\frac{F}{F + W \cdot \beta_w} - PDFF_{ex}\right)^2\right)$$

wherein $PDFF_{ex}$ is the proton density fat fraction measured in a separate experiment.

12. The method according to claim 11, wherein $PDFF_{ex}$ is provided by a separate 2-point Dixon experiment.

13. The apparatus according to claim 2, wherein R provides a quota between $F_{ref}$ and $PDFF_{ref}$ such that the method comprises the step of determining PDFF as:

$$\frac{F}{F_{ref}} \cdot \beta_f \cdot PDFF_{ref}$$

wherein
$F_{ref}$ is the fat signal in the reference tissue; and
$PDFF_{ref}$ is the PDFF of the reference tissue provided by a separate experiment of the reference tissue or by a predetermined constant.

14. The apparatus according to claim 2, wherein the T1 saturation factors of the fat signal in the reference tissue and in the ROI is equal, providing $\beta_f=1$.

15. The apparatus according to claim 13, wherein the processor is configured to determine PDFF from a fat-referenced two-point Dixon acquisition without previous correction for $T_2^*$ relaxation effects, and wherein the water signal in the reference tissue, $W_{ref}$, is low such that a resulting value when $W_{ref}$ is multiplied with a resulting $T_2^*$ relaxation effect provides an approximation that the water signal in the ROI equals an observed water signal in the ROI, $W_{2PD}$, being a reconstruction of the water signal from the MRI in the ROI using two-point Dixon acquisition, providing the PDFF to be determined by the processor as $$\frac{F_{2PD} - W_{2PD} \cdot \frac{e^{-T_{ip}/T_{2,w}^*} - e^{-T_{op}/T_{2,w}^*}}{2}}{F_{2PD,ref}} \cdot \beta_f \cdot PDFF_{ref}$$

wherein
$F_{2PD}$ is the observed fat signal in the ROI, being a reconstruction of the fat signal from the MRI in the ROI using two-point Dixon acquisition;

$T_{ip}$ is a constant of the echo time of the in-phase (IP) component comprising water plus fat signal of the water and fat signals from the MRI in the ROI;
$T_{2,w}^*$ is the $T_2^*$ relaxation effect of water in the ROI resulting from the two-point Dixon analysis;
$T_{op}$ is a constant of the echo time of the out-of-phase (OP) component comprising the difference between the water and fat signals from the MRI in the ROI; and
$F_{2PD,ref}$ is the observed fat signal of the reference tissue, being a reconstruction of the fat signal from the MRI in the reference tissue using two-point Dixon acquisition.

16. The apparatus according to claim 15, wherein the $T_2^*$ relaxation effect value is determined in a separate experiment.

17. The apparatus according to claim 15, wherein the $T_2^*$ relaxation effect value is set as a constant based on a population mean.

18. The apparatus according to claim 2, wherein the water and fat separated imaging is a spoiled gradient echo water-fat separated image reconstruction, and
wherein $\beta_f$ is the quota of $$\sin(\alpha)\frac{1 - e^{-T_R/T_{1f,ref}}}{1 - \cos\alpha\left(1 - e^{-T_R/T_{1f,ref}}\right)} \text{ and } \sin(\alpha)\frac{1 - e^{-T_R/T_{1f,ROI}}}{1 - \cos\alpha\left(1 - e^{-T_R/T_{1f,ROI}}\right)},$$

wherein $\alpha$ is the effective flip angle in the MRI acquisition, $T_R$ is the repetition time, $T_{1f,ref}$ is the T1 value for the fat signal in the reference tissue, and $T_{1f,ROI}$ is the T1 value for the fat signal in the ROI.

19. The apparatus according to claim 13, wherein the $F_{ref}$ is determined as a weighted interpolation of the fat signal in the reference tissue.

20. The apparatus according to claim 2, wherein R is defined as $F \cdot \beta_f + W \cdot \beta_w$, and wherein the T1 saturation factor of the fat signal in the reference tissue and in the ROI is equal, providing $\beta_f=1$, providing the processor to be configured to determine PDFF as $$\frac{F}{F + W \cdot \beta_w}$$

wherein
W is the water signal in the ROI provided by the MRI; and
$\beta_w$ is a function providing a ratio between the T1 saturation factor of the fat signal in the reference tissue and the T1 saturation factor of the water signal in the ROI.

21. The apparatus according to claim 20, wherein $\beta_w$ is determined in a separate experiment by determining $$\min_{\beta_w}\left(\sum_{Measurements}\left(\frac{F}{F + W \cdot \beta_w} - PDFF_{ex}\right)^2\right)$$

wherein $PDFF_{ex}$ is the proton density fat fraction measured in a separate experiment.

22. The apparatus according to claim 21, wherein $PDFF_{ex}$ is provided by a separate 2-point Dixon experiment.

* * * * *